United States Patent [19]

Callahan et al.

[11] Patent Number: 4,624,943

[45] Date of Patent: Nov. 25, 1986

[54] AROMATIC BASIC-TAILED VASOPRESSIN ANTAGONISTS

[75] Inventors: James F. Callahan, Philadelphia; Michael L. Moore, Media; Nelson C. Yim, Ambler, all of Pa.

[73] Assignee: SmithKline Beckman Corporation, Philadelphia, Pa.

[21] Appl. No.: 713,732

[22] Filed: Mar. 20, 1985

[51] Int. Cl.$^4$ .................. A61K 37/34; C07K 7/16
[52] U.S. Cl. .................................... 514/11; 514/807; 530/315
[58] Field of Search ............... 260/112.5 R; 514/11, 514/807; 530/315

[56] References Cited

U.S. PATENT DOCUMENTS 4,367,225  1/1983  Manning et al. ............. 260/112.5 R
4,399,125  8/1983  Manning et al. ............. 260/112.5 R
4,491,577  1/1985  Manning et al. ............. 260/112.5 R

OTHER PUBLICATIONS

M. Manning et al., Nature, 308 652 (1984).

Primary Examiner—Delbert R. Phillips
Attorney, Agent, or Firm—William H. Edgerton; Stuart R. Suter; Alan D. Lourie

[57] ABSTRACT

Certain new vasopressin-like peptides which have structures characterized by having a bisaminoalkylbenzene present in the vasopressin tail at the 7- or 8-position retain vasopressin antagonist activity. A species of the invention is [1-β-mercapto-β,β-cyclopentamethylenepropionic acid)-2-(O-ethyl)-D-tyrosine-4-valine-8-1',4'-bis(aminomethyl)benzene-9-desglycinamide]-vasopressin.

16 Claims, No Drawings

AROMATIC BASIC-TAILED VASOPRESSIN ANTAGONISTS

This invention relates to certain aromatic basic cyclic heptapeptides and hexapeptides which are vasopressin antagonists. More specifically, the structures of these cyclic peptides have a 1-($\beta$-mercapto)-propionic acid and five amino acid units cyclized into a 6-unit ring by means of a sulfur derived from the cysteine unit and a sulfur from the propionic acid unit. The ring has a distinguishing basic aromatic amino-alkyl or guanidinoalkyl tail which is attached via an amido linkage to the 6-cysteine unit of the ring, either directly or through another amino acid.

BACKGROUND OF THE INVENTION

M. Manning, W. H. Sawyer and coworkers have published a series of papers describing various [1-($\beta$-mercapto-$\beta,\beta$-cyclopentamethylenepropionic acid), 4-valine]-arginine-vasopressin congeners which have anti-vasopressin activity. Among these are Nature, 308 652 (1984), as well as U.S. Pat. Nos. 4,367,225, 4,399,125 and 4,491,577.

All of the Manning compounds have a peptide tail attached at unit 6 of the disulfide ring. The present compounds are distinguished over these by being hexapeptides which have an aromatic basic tail attached to unit 6 and which also have potent vasopressin antagonist activity.

We also have filed earlier U.S. patent applications, Ser. Nos. 673,824 filed Nov. 21, 1984 and 624,542 filed Aug. 28, 1984 which disclose $V_1$ and $V_2$ vasopressin antagonists, respectively, whose structures have non-aromatic alkyldiamines at the 7 or 8 position of the vasopressin structure.

None of the art, of which we are aware, discloses vasopressin antagonists which have a bulky, basic group in the tail portion of the VSP structure, such as an amine moiety which has an aromatic ring, and which still retain substantial antagonistic activity.

In the description herein and in the claims, the nomenclature common in the art of peptide and vasopressin chemistry is used. When no configuration is noted, the amino acid unit is in the L, or naturally occurring, form. In certain structural formulas, the thio members of the Cap and Cys units are added for clarity.

Certain of the peptide art designations used herein are the following: Cap, $\beta$-mercapto-$\beta,\beta$-cycloalkylenepropionic acid; Pmp, $\beta$-mercapto-$\beta,\beta$-cyclopentamethylenepropionic acid; Mpr, $\beta$-mercaptopropionic acid; dPen, $\beta$-mercapto, $\beta,\beta$-dimethylpropionic acid or desaminopenicillamine; Tyr(Alk), O-alkyltyrosine; Abu, $\alpha$-amino-n-butyric acid; Chg, cyclohexylglycine; Cha, cyclohexylalanine; Pba, $\alpha$-aminophenylbutyric acid; Gln, glutamic acid amide or glutamine; Gly, glycine; Tyr, tyrosine; Phe, phenylalanine; Phe(4'-Alk), 4'-alkylphenylalanine; N-MeAla, N-methylalanine; Val, valine; Ile, isoleucine; Nle, norleucine; Leu, leucine; Ala, alanine; Lys, lysine; Arg, arginine; Met, methionine; Asn, asparagine; Sar, sarcosine; Tos, tosylate; BHA, benzhydrylamine; DIEA, diisopropylethylamine; 4-MeBzl, 4-methylbenzyl; TFA trifluoroacetic acid; DCC, dicyclohexylcarbodiimide; Boc, t-butyloxycarbonyl; Z, benzyloxycarbonyl; VSP, vasopressin; HBT, hydroxybenzotriazole; ACM, acetamidomethyl; Mpa, non-cyclic $\beta$-mercaptopropionic acids.

"Alk" represents a lower alkyl of 1–4 carbons. For example, these may be optionally attached to the oxygen substituent of a tyrosine unit at position 2 or to the 4'-position of a Phe unit at position 3. Such alkyl substituents include methyl, ethyl, n-propyl, isopropyl or butyl. Ethyl is preferred. When the term, "vasopressin", is used, it means L-arginine vasopressin (AVP) unless otherwise modified. The 1-($\beta$-mercaptocycloalkylene)-propionic acid unit (Cap) at position 1 is often referred herein as Pmp for convenience since the pentamethylene containing unit is preferred. All the $\beta$-mercaptopropionic acids may be, at times, referred to herein as Mpr.

DESCRIPTION OF THE INVENTION

The basic vasopressin antagonist compounds of this invention are illusted by the following structural formula:

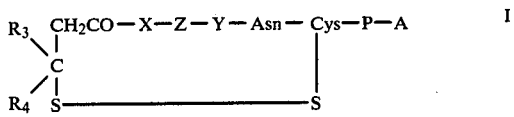

in which:

A is

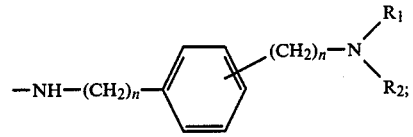

Z is Phe, Phe(4'-Alk), Tyr(Alk), Ile or Tyr;

X is a D or L isomer of Phe, Phe(4'-Alk), Val, Nva, Leu, Ile, Pba, Nle, Cha, Abu, Met, Chg, Tyr or Tyr(Alk);

P is D-Pro, L-Pro, $\Delta^3$-Pro, Ala, N-MeAla, Gly, Sar or a single bond;

Y is Val, Ile, Abu, Ala, Chg, Gln, Lys, Cha, Nle, Phe, Leu or Gly;

$R_1$ and $R_2$ are, each, hydrogen, $C_{1-5}$-alkyl; or, when one of $R_1$ or $R_2$ is hydrogen,

$R_3$ and $R_4$ are, each, hydrogen, methyl or, when taken together, a cycloalkylene ring of 4–6 members taken with the $\beta$-carbon to which they are attached; and n is an integer from 1–3; or a pharmaceutically acceptable, acid addition salt thereof.

A subgeneric group of compounds of this invention comprises compounds of formula I in which n is 1, $R_1$ and $R_2$ are both hydrogen. In formula I, substitution on the phenyl in the tail or side chain is preferably limited to the 1,3 or 1,4-position.

Also included in this invention are addition salts and complexes of the compounds of this invention, especially the nontoxic, pharmaceutically acceptable salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The end products of formula I have an additional strong basic group in their structures, therefore, their acid addition salt derivatives are easily prepared.

The compounds of formula I are prepared by the following reaction:

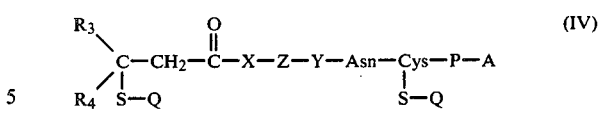

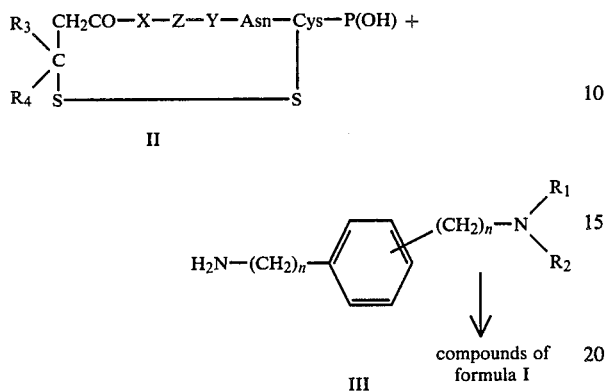

in which X, Z, Y, n, P and $R_{1-4}$ are as defined above for structure I, optionally in protected form as known to the art.

The dibasic compound (III) is used in the chemical reaction in a protected form at one of the two basic centers, if necessary. For example, a compound whose structure has an amino (—NH$_2$) or a secondary amino (—NHR), is reacted conveniently as the Boc derivative. When guanidino is present in its structure, reactant III is reacted as a tosylate derivative as known to the art. Other amino protecting groups, which are known to the art, may be used alternatively. When the terminal amine is tertiary such as with a dimethylamino or diethylamino group present, protective groups are not necessary.

The reaction of the starting material carboxylic acid (II) with the base (III) is carried out using any amide forming reaction common in the peptide art. For example, sustantially equimolar quantities of the two starting materials are reacted in the presence of a carbodiimide, such as dicyclohexylcarbodiimide or 1-(3-dimethylaminopropyl)-3-ethylcarbodiimide as the methiodide or hydrochloride in an aqueous or organic solvent respectively, plus 1-hydroxybenzotriazole in an organic solvent at room temperature until the reaction is complete.

The protective groups are, then, removed by methods known to the art such as reaction in the presence of trifluoromethanesulfonic acid and trifluoroacetic acid-/anisole at room temperature for the tosylate (guanidine) or reaction using trifluoroacetic acid in the cold for the Boc (amine) protecting groups.

The guanidino congeners may also be prepared from their amino counterparts directly by reaction of the latter with a compound such as a O-methylisourea. The reaction is usually carried out at a moderately basic pH, in an aqueous solution in the cold, until the rection is complete.

The starting materials (II) for the reaction described above or the end products (I) are prepared by oxidation of the following linear heptapeptide:

in which X, Z, Y, P and $R_{3-4}$ are as defined for formula I above and A is either OH or as defined for formula I above. The mercapto groups are members of the units at positions 1 and 6. Each Q is hydrogen or a displaceable group such as acetamidomethyl (ACM). The dithiol of formula IV may be also oxidized in the form of an ester or amide derivative of the unit at position 6 or 7. For example, the amide may be —NHR, —NH$_2$ or an A-containing amide derivative. The latter, as defined for structure I, gives the end products directly after cyclization and after removal of any protective groups.

Said oxidation is carried out using an excess of an alkali metal ferricyanide, such as potassium or sodium ferricyanide, with the linear intermediate IV. A suitable unreactive solvent, preferably an aqueous-miscible solvent at a neutral pH, about 7-7.5, is used. Reaction is carried out at ambient temperature or lower until the reaction is substantially complete. Preferably, the concentrations of the linear peptide dimercaptan and the oxidizing agent are low, say 0.01-0.1 molar concentration of oxidizing agent in several liters of aqueous solution to cyclize 1-5 grams of dimercaptan.

Other mild oxidation agents having an oxidation potential roughly equivalent to ferricyanide may also be used for the ring closure reaction. Oxygen passage through the reaction solution for several days or iodine in methanol are such alternatives. Cyclization, also, occurs when a displaceable, thiol-protective group such as that at the mercaptan group of the Pmp unit is displaced intramolecularly. An especially useful thio protective group is acetamidomethyl (ACM). Iodine/alcohol is used for direct, one-pot cyclization of the bis-ACM S-linear peptide. Of course, one skilled in the art will recognize that certain cyclization methods are not appropriate if an interfering reaction site is present in the structure of the starting material of formula IV. The linear mercaptan starting material may have common protective groups temporarily present at the various linear units.

The peptide chain of the linear peptides is usually built up, stepwise, proceeding from the P unit and working toward the Mpa unit. Each unit is properly protected as known in the peptide art and as described below. The sequence of step-reactions is conveniently carried out in a Beckman 990B peptide synthesizer or its equivalent without isolation of each intermediate peptide. The details of the procedure are in the working examples presented hereinafter.

The various amino acids (AA), which are consecutively added to the resin-supported chain, are protected as known to the art. For example, the Boc protecting group is used for an amino group, especially at the α-position; an optionally substituted benzyl, for the mercapto groups at the Cap and Cys units; tosyl for the Arg unit; and an optionally substituted carbobenzoxy (Z) for the Tyr or Lys units. The protective groups should, most conveniently, be those which are easily removed, that is, using acid treatment for the Boc group, sodium-liquid ammonia or catalytic hydrogenation for the benzyl or carbobenzoxy groups.

The resin supported peptide is treated with an excess of anhydrous hydrogen fluoride with an appropriate scavenger compound, such as anisole, to give the linear peptide intermediate of formula IV in good yield.

The end compounds of the invention have $V_1$ and/or $V_2$ vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors ($V_2$-receptors) located on the plasma membrane of certain renal epithelial cells. The most notable pharmacodynamic effect of the ADH antagonists of the invention is that of a water diuretic rather than of a natriuretic such as hydrochlorothiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease. The compounds of formula I in which $R_3$ and $R_4$ form a 5 or 6 membered ring are especially potent $V_2$-antagonists.

The second group of vasopressin receptor sites are the vascular pressor sites ($V_1$-receptors) within the cardiovascular system itself. These may also be antagonized by the compounds of this invention. The congeners of formula I in which $R_3$ and $R_4$ are hydrogen or methyl are potent $V_1$-antagonists. These compounds also have substantial anti-oxytocic activity as do all the compounds here described to some extent.

The compounds of this invention, therefore, are used especially to induce anti-hypertensive, anti-oxytocic or diuretic activity in patients in need of such treatment by administering internally, parenterally or by insufflation, a nontoxic but effective therefor quantity of the chosen compound, preferably dispersed in a pharmaceutical carrier. Dosage units of the active ingredient are selected from the range of 0.05 to 10 mg/kg, preferably 0.1 to 5 mg/kg, of base based on a 70 kg patient. The dosage units are administered to the human or animal patient from 1 to 5 times daily.

The pharmaceutical composition, which contains an active antagonist ingredient of formula I, comprises a dosage unit which is dissolved or suspended in a standard liquid carrier, such as isotonic saline, and is contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparation, gels, buffers for isotonic preparations, emulsions or aerosols.

$V_2$-antagonistic activity toward the natural anti-diuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopressin binding activity are described by F. Stassen et al., J. Pharmacology and Experimental Therapeutics, 223, 50-54 (1982). $V_1$-antagonistic activity is determined by procedures using the rat thoracic aorta tissue and plasma membranes of rat liver. These procedures are described in the noted publication and in a publication at the 1st International Conference on Diuretics, Miami, Fla., March (1984). Oxytocin antagonism is determined as described by W. Sawyer et al., Endocrinology, 106, 81 (1979).

The assay for anti-ADH activity in vivo is the hydropenic rat protocol described below:

Hydropenic Rat Screen

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/Kg $H_2O$. A tolerance test is used to determine significance. $ED_{300}$ is defined as the dose of compound ($\mu$g/kg) required to lower urine osmolality to 300 m-Osmoles/kg.

TABLE 1

A. [1-($\beta$-Mercapto-$\beta$,$\beta$-cyclopentamethylenepropionic acid)-2-(O-ethyl)-D-tyrosine-4-valine-8-1',3'-bis-(aminomethyl)benzene-9-desglycinamide]-vasopressin; $ED_{300}$, 77 $\mu$g/kg.

B. [1-($\beta$-Mercapto-$\beta$,$\beta$-cyclopentamethylenepropionic acid)-2-(O-ethyl)-D-tyrosine-4-valine-8-(1',5'-diaminopentane)-9-desglycinamide]-vasopressin; $ED_{300}$, 94.5 $\mu$g/kg.

C. [1-($\beta$-Mercapto-$\beta$,$\beta$-cyclopentamethylenepropionic acid)-2-(O-ethyl)-D-tyrosine-4-valine-8-desarginine-9-desglycinamide]-vasopressin; $ED_{300}$, >182 $\mu$g/kg.

D. [1-($\beta$-Mercapto-$\beta$,$\beta$-cyclopentamethylenepropionic acid)-2-(O-ethyl)-D-tyrosine-4-valine-8-1',4'-bis-(aminomethyl)benzene-9-desglycinamide]-vasopressin; $ED_{300}$, 195 $\mu$g/kg.

The following examples are intended solely to teach the preparation of the compounds of this invention. The temperatures are in degrees Centigrade.

EXAMPLE 1

Procedure for the general synthesis of the cyclic acid intermediates (II):

Boc-Pro-Merrifield resin was made by coupling Boc-Pro to Merrifield resin using the cesium salt method to give Boc-Pro-OCH$_2$C$_6$H$_4$-resin which was used as the starting material for the synthesis. The synthesis was carried out on the Beckman 990B peptide synthesizer using the following protocol. Three equivalents of the amino acids were dissolved in their appropriate solvents [the Boc derivatives of 4MeBzl-Cys, Val, Phe and 4-MeBzl-Pmp in methylene chloride, Asn in dimethylformamide, X such as D-Tyr(Et) or BrZ-D-Tyr in 1:1 methylene chloride/dimethylformamide] and were coupled using an equimolar amount of dicyclohexylcarbodiimide (DCC) and 1-hydroxybenzotriazole (HBT) except for the coupling of 4-MeBzl-Pmp where 1.0 equivalent of dimethylaminopyridine was used as catalyst. The extent of coupling was determined by qualitative ninhydrin analyses of each aliquot sample and couplings were repeated when necessary. The Boc groups were removed using 1:1 trifluoroacetic acid/methylene chloride and, after washing, the free amine was generated using 5% diisopropylethylamine/methylene chloride. The sequence of the peptide was checked before the addition of the 4MeBzl-Pmp and its homogeneity was confirmed. After the final coupling, the peptide was dried to give 2.24 g of peptide resin in the case of the D-Tyr(Et)$^2$-Pro$^7$-compound.

1.1 Grams (0.5 mmole) of the D-Tyr(Et)$^2$ peptide resin with 3 ml of anisole was stirred 60 min. at 0° (ice bath) in 25 ml of anhydrous liquid hydrogen fluoride (HF). The HF was, then, removed under reduced pressure at 0°. The residue was washed with ethyl ether (4×20 ml, discarded) and the peptide eluted with dimethylformamide (3×10 ml), 20% acetic acid (3×10 ml) and 0.3N ammonium hydroxide (3×10 ml). The filtrate was added to 2 l of degassed water and the pH adjusted to 7.1 with conc. ammonium hydroxide. A 0.01M solution of potassium ferricyanide was then added dropwise with stirring until a faint yellow color persisted (41 ml). The resultant solution was then passed through a flash column (5 cm×15 cm) of a packing of silica gel coated with an octadecylsilane (C-18). The column was, then, washed with 350 ml of water and the peptide eluted with 500 ml of 1:1 acetonitrile/water (0.25% trifluoroacetic acid) in 20 ml fractions. Fractions 11–17 were combined and concentrated. The residue was dissolved in conc. acetic acid, diluted with water and lyophillized to yield 189 mg of the D-Tyr(Et)$^2$-Pro$^7$ peptide, which was used without further purification for the synthesis of the tail modified peptides. The D-Tyr$^2$ congener was prepared similarly.

EXAMPLE 2

1,3-Bis-(aminomethyl)benzene (15 ml, 113.7 mmol) was dissolved in methylene chloride (100 ml) and was treated at room temperature with di-tert-butyl dicarbonate (8.72 ml, 37.9 mmol). The resulting solution was stirred at room temperature for 24 hours. The reaction mixture was diluted with chloroform, washed with water, dried (MgSO$_4$) and evaporated. The crude residue was dissolved in a minimum of 1 N hydrochloric acid and washed with chloroform. The aqueous fraction was made basic (pH=9) with solid sodium carbonate and was extracted with ethyl acetate, dried (MgSO$_4$) and evaporated to give 1.81 g (20%) of the pure mono-Boc derivative whose structure was confirmed by $^1$H nuclear magnetic resonance (NMR) and CI-mass spectra (MS) [(M+H)$^+$=237].

The mono-Boc intermediate (20 mg, 0.0864 mmol) and the 2-D-Tyr(Et)-4-Val-7-Pro acid from Example 1 (20 mg, 0.0216 mmol) in dimethylformamide (1 ml) were treated with HBT (9 mg, 0.0648 mmol) and DCC (7 mg, 0.0324 mmol) at room temperature for 114 hr. The reaction mixture was stripped to dryness and the residue treated with trifluoroacetic acid (5 ml) at room temperature for 4 hr. After the volatiles were removed under reduced pressure, the residue was taken into 10% acetic acid, filtered and passed over a BioRex 70 (H$^+$) ion exchange column. The basic products were washed off the ion exchange column with pyridine buffer (water/pyridine/acetic acid, 60:30:4) and evaporated. Final purification by preparative high pressure liquid chromatography (5μ Ultrasphere ODS) gave 10 mg (44%) of pure [1-(β-mercapto-β,β-cyclopentamethylene propionic acid)-2-(O-ethyl)-D-tyrosine-4-valine-8-1',3'-bis-(aminomethyl)benzene-9-desglycinamide]-vasopressin. The structure of the product was confirmed by FAB-MS [(M+H)$^+$=1042], [(M−H)$^-$=1040] and its purity confirmed by HPLC [(5μ Ultrasphere ODS, 4.6×250 mm) 55:45:0.1, H$_2$O/CH$_3$CN/TFA, eluted at 12.2 min.; gradient 80:20 to 50:50, H$_2$O/CH$_3$CN/0.1% TFA, eluted at 25.4 min].

EXAMPLE 3

1,4-Bis(aminomethyl)benzene (10 g, 73.4 mmol) was dissolved in methylene chloride (150 ml) and was treated at room temperature with di-tert-butyl dicarbonate (5.62 ml, 24.5 mmol) and the resulting solution was stirred at room temperature for 46 hr. The reaction was then diluted with chloroform, washed with water, dried (MgSO$_4$) and evaporated. The residue was dissolved in a minimum of 1N hydrochloric acid, washed with chloroform, made basic with solid sodium carbonate (pH=9) and extracted with ethyl acetate. The ethyl acetate extracts were combined, dried (MgSO$_4$) and evaporated to give pure mono-Boc-1,4-bis(aminomethyl)benzene whose structure was confirmed by $^1$H NMR and CI-MS [(M+H)$^+$=237].

The mono-Boc-1,4-bis(aminomethyl)benzene (20 mg, 0.0864 mmol) and 2-D-Tyr(Et)-7-Pro acid from Example 1 (20 mg, 0.0216 mmol) in dimethylformamide (1 ml) were treated with HBT (9 mg, 0.0648 mmol) and DCC (7 mg, 0.0324 mmol) at room temperature for 92 hr. The reaction mixture was stripped to dryness and the residue treated with TFA (5 ml) at room temperature for 3 hr. After the TFA had been removed under reduced pressure, the residue was taken into 1% acetic acid, filtered and passed over a BioRex 70 (H$^+$) ion exchange column. The basic products were washed off the ion exchange column with pyridine buffer (H$_2$O/pyridine/acetic acid, 66:30:4) and evaporated. Final purification by prep. HPLC (5μ Ultrasphere ODS) gave 9 mg of pure [1-(β-mercapto-β,β-cyclopentamethylenepropionic acid)-2-(O-ethyl)-D-tyrosine-4-valine-8-1',4'-bis-(aminomethyl)benzene-9-desglycinamide-vasopressin. The structure of the product was confirmed by FAB-MS [(M+H)$^+$=1042], [(M−H)$^-$=1040] and its purity confirmed by HPLC [(5μ Ultrasphere ODS, 4.6×250 mm): 55:45:0.1, H$_2$O/CH$_3$CN/TFA, eluted at 8.40 min; gradient 80:20 to 50:50, H$_2$O/CH$_3$CN/0.1% TFA, eluted at 25.5 min].

EXAMPLE 4

Mono-Boc-1,4-bis(aminomethyl)benzene (1.6 g, 6.6 mmol) in dioxane (2 ml) and water (6.5 ml) is treated with O-methylisourea hydrogen sulfate (1.25 g, 7.3 mmol) and 2N sodium hydroxide (aq) (3.75 ml) at room temperature. The resulting solution is stirred for 6 days. The solvent is removed under reduced pressure and the residue made basic (pH=12) by the addition of 2N sodium hydroxide. The residue is again evaporated, taken up in ethyl acetate, filtered and evaporated. The crude guanidine is dried by evaporation from toluene and used without further purification.

Crude guanidine (500 mg) in 2N sodium hydroxide (aq) (2 ml) and water (2 ml) is treated at room temperature with p-toluenesulfonyl chloride (516 mg, 2.70 mmol) for 18 hours. The pH is adjusted to 8 with 5% sodium carbonate solution. The mixture is extracted with ethyl acetate to give, upon evaporation, the tosyl Boc compound. Purification by flash chromatography (3×15 cm silica bed, 80% ethyl acetate/hexane) gives the desired tosylated product.

The tosyl-guanidino-boc-amine (125 mg) in methylene chloride (1 ml) is treated with trifluoroacetic acid (1 ml) at 0° for 40 minutes. The reaction is evaporated under vacuum, the residue's pH adjusted to 8 with 5% sodium carbonate solution and evaporated to dryness.

The residue is taken up into ethyl acetate, filtered and evaporated. The crude des-Boc product is dried by evaporation from toluene.

[1-(β-Mercapto-β,β-cyclopentamethylenepropionic acid-2-(O-ethyl)-D-tyrosine-4-valine-8-desarginine-9-desglycinamide]-vasopressin (35 mg, 0.038 mmol), prepared as in Example 1, in dimethyulformamide (0.5 ml) is treated at room temperature with the tosyl-guanidino amine (49 mg, 0.114 mmol), DCC (12 mg, 0.057 mmol) and HBT (8 mg, 0.057 mmol). The mixture is stirred for 43 hours. The solvent is removed at reduced pressure and the residue is dissolved in trifluoroacetic acid (2 ml), then treated at room temperature with trifluoromethanesulfonic acid (150 μl, 1.7 mmol) and anisole (37 μl) with stirring for 2 hours. The reaction mixture is evaporated to dryness, dissolved in 10% acetic acid, filtered and passed through a BioRex-70 (H+) column. The crude guanidine is eluted off the column with pyridine buffer (pyridine/water/acetic acid, 30:66:4), evaporated and the residue purified by preparative HPLC (5μ ODS, $CH_3CN/H_2O$/TFA 40:60:0.25%) to give [1-(β-mercapto-β,β-cyclopentamethylenepropionic acid)-2-(O-ethyl)-D-tyrosine-4-valine-8-(1'-aminomethyl-4'-quanidinomethylbenzene)-9-desglycinamide]-vasopressin.

EXAMPLE 5

A solution of the L-Phe²-proline acid (0.042 mmol) prepared as in Example 1, and mono-Boc-1,4-bis(aminoethyl)benzene (0.129 mmol) in dimethylformamide (900 μl) is treated with dicyclohexylcarbodiimide (13 mg, 0.065 mmol) and 1-hydroxybenzotriazole hydrate (9 mg, 0.065 mmol) with stirring at room temperature for 43 hours. The dimethylformamide is, then, removed under vacuum. The residue is treated with trifluoroacetic acid at 0° for 1 hour. After this time, the trifluoroacetic acid is removed under vacuum and the residue in 1% acetic acid was passed through a BioRex 70 (H+) ion exchange column. The basic products are washed off the column with pyridine buffer ($H_2O$/pyridine/acetic acid, 66:30:4) and evaporated. Final purification by prep HPLC (5μ Ultrasphere ODS) gives [1-(β-mercapto-β,β-cyclopentamethylenepropionic acid)-2-phenylalanine-4-valine-8-1',4'-bis(aminoethyl)benzene-9-desglycinamide]-vasopressin.

EXAMPLE 6

O-Methylisourea hydrogen sulfate (88 mg, 0.511 mmol) is dissolved in water (3 ml) and the pH adjusted to 10 using 3N NaOH(aq). Then, [1-(β-mercapto-β,β-cyclopentamethylenepropionic acid)-2-(O-ethyl)-D-tyrosine-4-valine-8-1',3'-bis(aminomethyl)benzene-9-desglycinamide]-vasopressin from above (8.7 mg, 8.35 mmol) is added in water (2 ml). The pH is corrected to 10 and the solution is kept in the refrigerator for 17 days. The pH of the solution is adjusted to 4.5 with 1% HOAc(aq). The solution is stripped, taken up in 1:1 $H_2O/CH_3CN$ and purified by preparative HPLC (5μ ODS) to give [1-(β-mercapto-β,β-cyclopentamethylenepropionic acid)-2-(O-ethyl)-D-tyrosine-4-valine-8-(1'-aminomethyl-3'-guanidinomethylbenzene)-9-desglycinamide]-vasopressin.

EXAMPLE 7

Synthesis of Pmp—D-Tyr(Et)—Phe—Val—Asn—Cys(OH):

The title compound was prepared by means of the solid phase preparation described in Example 1 but using Boc-Cys-Merrifield resin as starting material which was subsequently coupled with the appropriate Boc-amino acid sequentially, followed by hydrogen fluoride deprotection, cleavage from the resin concurrently and, then, oxidative cyclization were carried out as described. Purification was achieved first by $C_{18}$ flash column chromatography followed by preparative high pressure liquid chromatography (HPLC) to yield 65 mg of Cys acid peptide from 0.5 mmoles of resin (16% yield). The structure was confirmed by amino acid analysis: Asp, 1.00; Cys, 0.47; Val, 0.96; Tyr, 0.98; Phe, 0.94 and FAB-MS $(M+H)^+=827$, $(M-H)^-=825$. Purity was confirmed by HPLC (5μ Ultrasphere ODS, 60:40:0.1, $H_2O:CH_3CN:TFA$).

EXAMPLE 8

A solution of 32.6 mg (0.039 mmol) of the D-Tyr(Et)-cysteine acid, prepared as in Example 7, and mono-t-Boc-1,3-bis(aminomethyl)benzene (28 mg, 0.118 mmol) in dimethylformamide (1 ml) is treated with dicyclohexylcarbodiimide (12 mg, 0.059 mmol) and 1-hydroxybenzotriazole hydrate (8 mg, 0.059 mmol) and stirred at room temperature for 90 hours. The dimethylformamide is then removed under vacuum. The residue is treated with trifluoroacetic acid (5 ml) at 0° for 3 hours. After this time, the trifluoroacetic acid is removed under vacuum and the residue therefrom dissolved in 10% acetic acid and lyophilized. The crude lyophilate is purified by prep HPLC (5μ Ultrasphere ODS, 60:40:0.1/$H_2O:CH_3CN:TFA$) to give [1-(β-mercapto-β,β-cyclopentamethylenepropionic acid)-2-(O-ethyl)-D-tyrosine-4-valine-7-1',3'-bis(aminomethyl)benzene-8-desarginine-9-desglycinamide]-vasopressin.

EXAMPLE 9

Procedure for the general synthesis of the propionic acid intermediates (II, $R_3$ and $R_4$=H or $CH_3$):

Boc-Pro-Merrifield resin was made by coupling Boc-Pro to Merrifield resin using the cesium salt method to give Boc-Pro-$OCH_2C_6H_4$-resin which was used as the starting material for the synthesis. The synthesis was carried out on the Beckman 990B peptide synthesizer using the following protocol. Three equivalents of the amino acids were dissolved in their appropriate solvents [the Boc derivatives of 4-MeBzl-Cys, Val, Phe and 4-MeBzl-Mpa in methylene chloride, Asn in dimethylformamide, D-Tyr(Et) or Bzl-D-Tyr in 1:1 methylene chloride/dimethylformamide] and were coupled using an equimolar amount of dicyclohexylcarbodiimide (DCC) and 1-hydroxybenzotriazole (HBT) except for the coupling of 4-MeBzl-Mpa where 1.0 equivalent of dimethylaminopyridine was used as catalyst. The extent of coupling was determined by qualitative ninhydrin analyses of each aliquot sample and couplings were repeated when necessary. The Boc groups were removed using 1:1 trifluoroacetic acid/methylene chloride and, after washing, the free amine was generated using 5% diisopropylethylamine/methylene chloride. The sequence of the peptide was checked using solid phase sequencing before the coupling of the 4-MeBzl-Mpa and its homogeneity confirmed. After the final coupling, the peptide resin was dried and used as such in the cyclization.

The 1-Mpa peptide resin (0.5 mmol) with 3 ml of anisole was stirred for 60 minutes at 0° (ice bath) in 25 ml of anhydrous liquid hydrogen fluoride (HF). The HF was then removed under reduced pressure at 0°. The residue was washed with ethyl ether (4×20 ml, discarded) and the peptide eluted with dimethylformamide (3×10 ml), 20% acetic acid (3×10 ml) and 0.3N ammonium hydroxide (3×10 ml). The filtrate was added to 2 l of degassed water and the pH adjusted to 7.1 with conc. ammonium hydroxide. A 0.01M solution of potassium ferricyanide was then added dropwise with stirring until a faint yellow color persists. The resulted solution was then passed through a flash column (5 cm×15 cm) of a packing of octadecylsilane ($C_{18}$) bonded to silica gel. The column was, then, washed with 350 ml of water and the peptide eluted with 500 ml of 1:1 acetonitrile/water (0.1% trifluoroacetic acid) in 20 ml fractions. The residue from the product containing eluants was dissolved in conc. acetic acid, diluted with water and lyophilized to give the cyclized acid intermediate, which was used without further purification for the synthesis of the basic tail modified peptides.

A. Identification of [1-desaminopenicillamine-2-(O-methyl)-tyrosine-8-desarginine-9-desglycinamide]-vasopressin.

A total of 183 mg of pure titled 1-desaminopenicillamine intermediate was obtained from a 1 mmole run as described above. Purification was by: (1) $C_{18}$-flash column chromatography, (2) CCD, and (3) gel filtration. Its structure was confirmed by FAB-MS; $(M+H)^+ = 899$, $(M-H)^- = 897$ and amino acid analysis: Asp, 1.03; Pro, 0.97; Phe, 0.95; Glu, 1.00; Tyr, 0.79. The purity was confirmed by HPLC (5μ, $C_{18}$ column, linear gradient, 80:20 to 50:50, $H_2O/CH_3CN$:0.1% TFA, 30 min, eluted at 33.01 min).

B. Identification of [1-mercaptopropionic acid-2-(O-ethyl)-D-tyrosine-3-isoleucine-4-threonine-8-desarginine-9-desglycinamide]-vasopressin.

A total of 290 mg of pure titled heptapeptide intermediate was obtained from a 1 mmole run as described above. Purification was as described. Its structure was confirmed by FAB-MS; $(M+H)^+ = 822$ and amino acid analysis: Asp, 1.00; Pro, 1.05; Ile, 0.91; Thr, 0.97; Cys, 0.30; Tyr, 0.91. The purity was confirmed by HPLC (5μ, $C_{18}$ column, linear gradient, 80:20 to 50:50, $H_2O:CH_3CN$:0.1% TFA, 30 min, eluted at 27.6 min).

EXAMPLE 10

To a solution of the proline intermediate from Example 9A, (40 mg, 0.044 mmol) and mono-Boc-1,4-bis-(aminomethyl)benzene (50 mg, 0.212 mmol) in dimethylformamide (2 ml), dicyclohexylcarbodiimide (14.0 mg, 0.07 mmol) and 1-hydroxybenzotriazole hydrate (9.0 mg, 0.07 mmol) are added. The reaction mixture is stirred at room temperature for 90 hours. The dimethylformamide is, then, removed under vacuum. The residue is treated with trifluoroacetic acid (6 ml) at room temperature for 2 hours. After this time, the trifluoroacetic acid is removed under vacuum and the residue in 1% acetic acid is passed over a BioRex 70 (H+) ion exchange column. The basic products are washed off the ion exchange column with pyridine buffer ($H_2O$/pyridine/HOAc, 66:30:4) and evaporated. Subsequent purification by prep HPLC (5μ Ultrasphere ODS) gave [1-desaminopenicillamine-2-(O-methyl)-tyrosine-8-1',4'-bis-(aminomethyl)benzene-9-desglycinamide]-vasopressin.

EXAMPLE 11

A solution of 80 mg (0.097 mmol) of the proline acid of Example 9B and 4-dimethylaminomethyl-1-aminomethylbenzene (0.335 mmol) in dimethylformamide (3 ml) is treated with dicyclohexylcarbodiimide (30 mg, 0.146 mmol) and 1-hydroxybenzotriazole hydrate (39 mg, 0.291 mmol), then stirred at room temperature for 48 hours. The dimethylformamide is removed under vacuum and the residue is purified by prep HPLC to give [1-(β-mercaptopropionic acid)-2-(O-ethyl)-D-tyrosine-3-isoleucine-4-threonine-8-(4'-dimethylaminomethyl-1'-aminomethylbenzene)-9-desglycinamide]-vasopressin.

EXAMPLE 12

[1-Desaminopenicillamine-2-(O-methyl)-tyrosine-7-desproline-8-desarginine-9-desglycinamide]-vasopressin is prepared by means of solid phase as described in Example 9 but using Boc-Cys-Merrifield resin as starting material which is subsequently coupled with the appropriate Boc-amino acids sequentially, followed by hydrogen fluoride deprotection, cleavage from the resin concurrently and, then, oxidative cyclization. Purification is carried out as described in Example 9.

EXAMPLE 13

A solution of 0.043 mmoles of the cysteine acid, prepared as in Example 12, and mono-Boc-1,4-bis-(aminomethyl)benzene (0.129 mmol) in dimethylformamide (1 ml) is treated with dicyclohexylcarbodiimide (13 mg, 0.065 mmol) and 1-hydroxybenzotriazole hydrate (9 mg, 0.065 mmol) and is stirred at room temperature for 48 hours. The dimethylformamide is then removed under vacuum. The residue is treated with trifluoroacetic acid (5 ml) at room temperature for 3 hours. After this time, the trifluoroacetic acid is removed under vacuum and the residue therefrom dissolved in 10% acetic acid, then passed through a BioRex 70 (H+) ion exchange column. The basic products are washed off the ion exchange column with pyridine buffer (water/pyridine/acetic acid, 66:30:4) and evaporated to dryness to give [1-β-desaminopenicillamine-2-(O-methyl)-tyrosine-7-1',4'-bis(aminomethyl)benzene-8-desarginine-9-desglycinamide]-vasopressin.

EXAMPLE 14

Substituting the appropriate protected amino acids in the above synthetic sequence gives the respective cysteine-6 or proline-7 acids, the basic aromatic-tailed peptide end products or a salt thereof as follows:

a. [1-desaminopenicillamine-2-(O-ethyl)-D-tyrosine-3-(4'-methyl)phenylalanine)-7-D-proline-8-1',4'-bis-(aminomethyl)benzene-9-desglycinamide]-vasopressin sulfate;

b. [1-mercaptopropionic acid-2-(O-ethyl)-D-tyrosine-4-(α-aminobutyric acid)-7-(N-methyl-alanine)-8-1',4'-bis(aminomethyl)benzene-9-desglycinamide]-vasopressin;

c. [1-(β-mercaptopropionic acid)-2-valine-4-cyclohexylglycine-7-sarcosine-8-1',3'-bis(aminomethyl)benzene-9-desglycinamide]-vasopressin hydrochloride;

d. [1-(β-mercaptopropionic acid)-4-glutamine-8-1',3'-bis(aminomethyl)benzene-9-desglycinamide]-vasopressin;
e. [1-desaminopenicillamine-2-phenylalanine-7-(1'-aminomethyl-4'-guanidinomethyl)benzene-8-desarginine-9-desglycinamide]-vasopressin;
f. [1-desaminopenicillamine-2-D-α-aminophenylbutyric acid-4-isoleucine-7-D-proline-8-1',4'-bis(aminomethyl)benzene-9-desglycinamide]-vasopressin;
g. [1-desaminopenicillamine-2-tryptophan-4-glutamine-7-1',4'-bis(aminomethyl)benzene-8-desarginine-9-desglycinamide]-vasopressin;
h. [1-(β-mercapto-β,β-cyclopentamethylenepropionic acid)-2-(O-ethyl)-D-tyrosine-3-(4'-methylphenylalanine)-7-D-proline-8-1',3'-bis(aminomethyl)benzene-9-desglycinamide]-vasopressin;
i. [1-(β-mercapto-β,β-cyclopentamethylenepropionic acid)-2-(O-ethyl)-D-tyrosine-4-(α-aminobutyric acid)-7-(N-methyl-alanine)-8-1',4'-bis(aminomethyl)benzene-9-desglycinamide]-vasopressin;
j. [1-(β-mercapto-β,β-cyclopentamethylenepropionic acid)-2-(O-ethyl)-D-tyrosine-4-cyclohexylglycine-7-L-sarcosine-8-1',3'-bis(aminomethyl)benzene-9-desglycinamide]-vasopressin.
k. [1-(β-mercapto-β,β-cyclopentamethylenepropionic acid)-4-glutamine-1',4'-bis(aminomethyl)benzene-9-desglycinamide]-vasopressin;
l. [1-(β-mercapto-β,β-cyclopentamethylenepropionic acid)-2-D-phenylalanine-4-valine-7-1',3'-bis-(aminomethyl)benzene-8-desarginine-9-desglycinamide]-vasopressin;
m. [1-(β-mercapto-β,β-cyclopentamethylenepropionic acid)-2-D-α-aminophenylbutyric acid-4-isoleucine-7-D-proline-8-1',4'-bis(aminomethyl)benzene-9-desglycinamide]-vasopressin;
n. [1-desaminopenicillamine-2-(O-ethyl)-D-tyrosine-4-valine-7-D-proline-8-1',3'-bis(aminomethyl)benzene-9-desglycinamide]-vasopressin;
o. [1-(β-mercapto-β,β-cyclopentamethylenepropionic acid)-2-(O-ethyl)-D-tyrosine-4-valine-7-D-proline-8-1',3'-bis(aminomethyl)benzene-9-desglycinamide]-vasopressin;
p. [1-mercaptopropionic acid-2-(O-ethyl)-D-tyrosine-3-isoleucine-4-threonine-7-D-proline-8-1',3'-bis-(aminomethyl)benzene-9-desglycinamide]-vasopressin.

EXAMPLE 15

Parenteral Dosage Unit Compositions:

A preparation which contains 0.10 mg of the basic peptide of Examples 2, 3 or 14 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The procedure is repeated as necessary, from 1–5 times daily, or in continuous i.v. drip injection.

Nasal Dosage Unit Compositions:

2.5 Mg of a finely ground basic peptide of this invention, such as the product of Example 2, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a cardiovascular subject from 1–6 times a day.

What is claimed is:

1. A vasopressin antagonist having the formula:

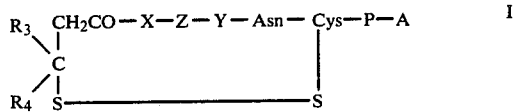

in which:

A is

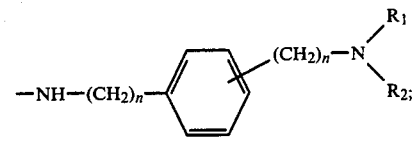

Z is Phe, Phe(4'-Alk), Tyr(Alk) Ile or Tyr;
X is a D or L isomer of Phe, Phe(4'-Alk), Val, Nva, Leu, Ile, Pba, Nle, Cha, Abu, Met, Chg, Tyr or Tyr(Alk);
P is D-Pro-, L-Pro, Δ³-Pro, L-Ala, N-L-MeAla, Gly, Sar or a single bond;
Y is Val, Ile, Abu, Ala, Chg, Gln, Lys, Cha, Nle, Phe, Leu or Gly;
$R_1$ and $R_2$ are, each, hydrogen, $C_{1-5}$-alkyl; or, when one of $R_1$ or $R_2$ is hydrogen,

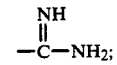

$R_3$ and $R_4$ are, each, hydrogen, methyl or, when taken together, a cycloalkylene ring of 4–6 members taken with the β-carbon to which they are attached; and
n is an integer from 1–3; or a pharmaceutically acceptable, acid addition salt thereof.

2. The compounds of claim 1 in which n is 1, $R_1$ is hydrogen and $R_2$ is hydrogen.

3. The compounds of claim 1 in which the substituent on the phenyl ring in A is at the 3 or 4-position.

4. The compound of claim 1 in which the compound is [1-(β-mercaptocyclopentamethylenepropionic acid)-2-(O-ethyl)-D-tyrosine-4-valine-8-1',3'-bis(aminomethyl)benzene-9-desglycinamide]-vasopressin or a pharmaceutically acceptable, acid addition salt thereof.

5. The compound of claim 1 in which the compound is [1-(β-mercapto-β,β-cyclopentamethylenepropionic acid)-2-(O-ethyl)-D-tyrosine-4-valine-8-1',4'-bis-(aminomethyl)benzene-9-desglycinamide]-vasopressin or a pharmaceutically acceptable, acid addition salt thereof.

6. The compound of claim 1 in which the compound is [1-desaminopenicillamine-2-(O-methyl)-L-tyrosine-8-1',4'-bis(aminomethyl)benzene-9-desglycinamide]-vasopressin or a pharmaceutically acceptable, acid addition salt thereof.

7. The compound of claim 1 in which the compound is [1-(β-mercaptopropionic acid)-2-(O-ethyl)-D-tyrosine-3-isoleucine-4-threonine-8-4'-dimethylaminomethyl-1'-aminomethylbenzene-9-desglycinamide]-vasopressin or a pharmaceutically acceptable, acid addition salt thereof.

8. The compound of claim 1 in which the compound is [1-(β-mercapto-β,β-cyclopentamethylenepropionic acid)-2-(O-ethyl)-D-tyrosine-4-valine-7-D-proline-8-1',3'-bis(aminomethyl)benzene-9-desglycinamide]-vasopressin or a pharmaceutically acceptable, acid addition salt thereof.

9. The compound of claim 1 in which the compound is [1-desaminopenicillamine-2-(O-ethyl)-D-tyrosine-4-valine-7-D-proline-8-1',3'-bis(aminomethyl)benzene-9-desglycinamide]-vasopressin or a pharmaceutically acceptable, acid addition salt thereof.

10. The compound of claim 1 in which the compound is [1-mercaptopropionic acid-2-(O-ethyl)-D-tyrosine-3-isoleucine-4-threonine-7-D-proline-8-1',3'-bis(aminomethyl)benzene-9-desglycinamide]-vasopressin or a pharmaceutically acceptable, acid addition salt thereof.

11. A pharmaceutical composition having vasopressin antagonist activity comprising a pharmaceutical carrier and, dispersed therein, an effective therefor but nontoxic quantity of a compound of claim 1.

12. A pharmaceutical composition having vasopressin antagonist activity comprising a pharmaceutical carrier and, dispersed therein, an effective therefor but nontoxic quantity of that compound of claim 4.

13. A pharmaceutical composition having vasopressin antagonist activity comprising a pharmaceutical carrier and, dispersed therein, an effective therefor but nontoxic quantity of the compound of claim 5.

14. The method of producing vasopressin antagonist activity in a patient in need thereof which comprises administering parenterally or intranasally to said patient an effective therefor, nontoxic quantity of a compound of claim 1.

15. The method of producing vasopressin antagonist activity in a patient in need thereof which comprises administering to said patient parenterally or intranasally an effective therefor, nontoxic quantity of the compound of claim 4.

16. The method of producing vasopressin antagonist activity in patient in need thereof which comprises administering to said patient parenterally or intranasally an effective therefor, nontoxic quantity of the compound of claim 5.

* * * * *